(12) United States Patent
Sazonov

(10) Patent No.: US 9,814,637 B2
(45) Date of Patent: Nov. 14, 2017

(54) PATIENT MONITORING SYSTEMS AND METHODS

(71) Applicant: The Board of Trustees of the University of Alabama, Tuscaloosa, AL (US)

(72) Inventor: Edward Sazonov, Northport, AL (US)

(73) Assignee: The Board of Trustees of The University of Alabama, Tuscaloosa, AL (US)

( * ) Notice: Subject to any disclaimer, the term of this patent is extended or adjusted under 35 U.S.C. 154(b) by 71 days.

(21) Appl. No.: 14/734,878

(22) Filed: Jun. 9, 2015

(65) Prior Publication Data

US 2015/0351981 A1  Dec. 10, 2015

Related U.S. Application Data

(60) Provisional application No. 62/010,199, filed on Jun. 10, 2014.

(51) Int. Cl.
    *A61G 5/10* (2006.01)
    *G01L 5/00* (2006.01)
    (Continued)

(52) U.S. Cl.
    CPC .......... *A61G 5/1043* (2013.01); *A61B 5/1036* (2013.01); *A61B 5/1118* (2013.01);
    (Continued)

(58) Field of Classification Search
    CPC .............. A61G 5/1043; A61G 7/05769; A61G 2203/32; A61G 2203/34; A61G 5/1045;
    (Continued)

(56) References Cited

U.S. PATENT DOCUMENTS

| 2002/0067273 | A1* | 6/2002 | Jaques | ..................... | A61B 5/11 340/573.4 |
| 2004/0082502 | A1* | 4/2004 | Gans | .................... | A61K 9/0095 424/443 |

(Continued)

OTHER PUBLICATIONS

Vaishampayan et al, Individualization of a Manualized Pressure Ulcer Prevention Program: Targeting Risky Life Circumstances Through Community-Based Intervention for People with Spinal Cord Injury. Adv Skin Wound Care, 2011, vol. 24: pp. 275-286.

(Continued)

*Primary Examiner* — George Bugg
*Assistant Examiner* — Thang Tran
(74) *Attorney, Agent, or Firm* — Meunier Carlin & Curfman LLC

(57) ABSTRACT

Various implementations of a patient monitoring assembly may be useful in preventing pressure ulcers, monitoring of air cushion inflation, estimating physical activity and energy expenditure and managing body weight of a patient seated on the assembly. The patient monitoring assembly may be installed on a manual or powered wheelchair, for example, and continuously monitors and provides feedback to the patient and/or caregiver about whether the patient is engaging in pressure relief activities while seated on a cushion of the assembly, whether the patient's activities are in accordance with clinical guidelines for pressure relief, the amount of calories expended over a period of time and the weight and weight distribution of the patient seated on the assembly. The feedback may be provided in substantially real time via an interface on the wheelchair and/or via a remotely located computing device.

22 Claims, 7 Drawing Sheets

(51) Int. Cl.
*A61B 5/00* (2006.01)
*A61B 5/103* (2006.01)
*A61B 5/11* (2006.01)
*A61G 7/057* (2006.01)

(52) U.S. Cl.
CPC .......... *A61B 5/6894* (2013.01); *A61G 5/1045* (2016.11); *G01L 5/00* (2013.01); *A61B 5/447* (2013.01); *A61G 7/05769* (2013.01); *A61G 2203/32* (2013.01); *A61G 2203/34* (2013.01)

(58) Field of Classification Search
CPC .. A61G 5/1036; A61G 5/1118; A61G 5/6894; A61G 5/447; A61B 5/1036; A61B 5/447; G01L 5/00
USPC .... 340/573.1, 286.07, 3.1, 517, 573.3, 5.61, 340/5.81, 691.6, 10.1–10.6, 572.1–572.9; 600/301, 309, 549, 306, 310, 336, 407, 600/534, 595
See application file for complete search history.

(56) References Cited

U.S. PATENT DOCUMENTS

| | | | | |
|---|---|---|---|---|
| 2004/0237203 | A1* | 12/2004 | Romano | A47C 27/122 5/713 |
| 2005/0121959 | A1* | 6/2005 | Kruse | A61G 5/006 297/330 |
| 2008/0120780 | A1* | 5/2008 | Genaro | A61G 7/05776 5/600 |
| 2010/0101026 | A1* | 4/2010 | Papaioannou | A61G 7/0573 5/710 |
| 2010/0225489 | A1* | 9/2010 | Hinterlong | A61B 5/103 340/573.4 |
| 2010/0298742 | A1* | 11/2010 | Perlman | A61B 5/1116 600/595 |
| 2011/0245732 | A1* | 10/2011 | Mravyan | A61B 5/1116 600/587 |
| 2013/0012786 | A1* | 1/2013 | Horseman | G06F 19/3418 600/301 |
| 2013/0267791 | A1* | 10/2013 | Halperin | A61B 5/002 600/300 |
| 2014/0145848 | A1* | 5/2014 | Amir | G08B 21/043 340/573.1 |
| 2014/0345058 | A1* | 11/2014 | Escobedo | A61G 7/05769 5/655.3 |
| 2014/0350434 | A1* | 11/2014 | Hovorka | A61B 5/0048 600/587 |
| 2015/0128354 | A1* | 5/2015 | Greenstein | A61G 5/128 5/710 |
| 2015/0290061 | A1 | 10/2015 | Stafford et al. | |

OTHER PUBLICATIONS

Bolton et al., Assessing the need for developing a comprehensive content-validated pressure ulcer guideline, Ostomy Wound Manage, 2008, vol. 54: pp. 22-30.
Schofield et al,. Reviewing the Literature on the Effectiveness of Pressure Relieving Movements. Nursing Research and Practice 2013.
Stinson et al., A literature review of pressure ulcer prevention: weight shift activity, cost of pressure care and role of the occupational therapist, The British Journal of Occupational Therapy, 2013, vol. 76: pp. 169-178.
Consortium for Spinal Cord Medicine Clinical Practice Guidelines. Pressure ulcer prevention and treatment following spinal cord injury: a clinical practice guideline for health-care professionals. J Spinal Cord Med, 2001, vol. 24 Suppl 1, S40-101.
Brienza et al., A Randomized Clinical Trial on Preventing Pressure Ulcers with Wheelchair Seat Cushions, Journal of the American Geriatrics Society, 2010, vol. 58: pp. 2308-2314.
Kozniewski et al., Wheelchair pressure monitoring alert system for the reduction of the occurrence of pressure sores, Bioengineering Conference (NEBEC), 2011 IEEE 37th Annual Northeast, pp. 1-2.
Dai et al., A robust wheelchair pressure relief monitoring system, 2012 Annual International Conference of the IEEE Engineering in Medicine and Biology Society (EMBC), 2012, pp. 6107-6110.
Bang et al. Body pressure measuring device for the prevention against pressure sores, Proceedings of the 4th International Convention on Rehabilitation Engineering & Assistive Technology 38:1-38:4 (Singapore Therapeutic, Assistive & Rehabilitative Technologies (START) Centre, 2010), at <http://dl.acm.org/citation.cfm?id=1926058.1926096>.
The ROHO Group—XSensor Interface Pressure Measurement, <http://www.therohogroup.com/products/xsensor%20systems/>.
i-Pressure Wheelchair Cushion Monitor—Wheelchair Diffusion, Wheelchair Diffusion, <http://www.usatechguide.org/blog/i-pressure-wheelchair-cushion-monitor/>.
Aquila Corporation Products, Wheelchair cushions—Pressure sore prevention and healing, <http://www.aquilacorp.com/products/>, accessed May 9, 2016.
Gupta et al., Body mass index in spinal cord injury—a retrospective study, Spinal Cord, 2006, vol. 44: pp. 92-94.
Tomey et al., Dietary intake and nutritional status of urban community-dwelling men with paraplegia, Arch Phys Med Rehabil, 2005, vol. 86: pp. 664-671.
Howard et al. Internal Invalidity in Pretest-Posttest Self-Report Evaluations and a Re-evaluation of Retrospective Pretests, Applied Psychological Measurement, 1979, vol. 3: pp. 1-23.
Spungen et al., Factors influencing body composition in persons with spinal cord injury: a cross-sectional study, J. Appl. Physiol., 2003, vol. 95: pp. 2398-2407.
Jones et al., Healthy body mass index values often underestimate body fat in men with spinal cord injury, Arch Phys Med Rehabil, vol. 84: pp. 1068-1071.
Knight et al., A Tool to Assess the Comfort of Wearable Computers, Human Factors: The Journal of the Human Factors and Ergonomics Society, 2005, vol. 47: pp. 77-91.
Rodriguez et al., The metabolic response to spinal cord injury, Spinal Cord 1997, vol. 35: pp. 599-604.
Monroe et al. Lower daily energy expenditure as measured by a respiratory chamber in subjects with spinal cord injury compared with control subjects, Am. J. Clin. Nutr., 1998, vol. 68: pp. 1223-1227.
Buchholz et al., Physical activity levels are low in free-living adults with chronic paraplegia, Obes. Res., 2003, vol. 11: pp. 563-570.
Hiremath et al., Evaluation of activity monitors in manual wheelchair users with paraplegia, J Spinal Cord Med 2011, vol. 34: pp. 110-117.
Warms et al., Measurement and description of physical activity in adult manual wheelchair users, Disabil Health J, 2008, vol. 1: pp. 236-244.
Froehlich-Grobe et al., Truth Be Told: Evidence of Wheelchair Users' Accuracy in Reporting Their Height and Weight, Archives of Physical Medicine and Rehabilitation, 2012, vol. 93: pp. 2055-2061.
Washburn et al., Assessing physical activity during wheelchair pushing: validity of a portable accelerometer, Adapted Physical Activity Quarterly, 1999, vol. 16: pp. 290-299.
Hiremath et al., Predicting Energy Expenditure of Manual Wheelchair Users With Spinal Cord Injury Using a Multisensor-Based Activity Monitor, Archives of Physical Medicine and Rehabilitation, 2012, vol. 93: pp. 1937-1943.
Ding et al., Universal Access in Human-Computer Interaction, Context Diversity (Stephanidis, C.) pp. 145-152 (Springer Berlin Heidelberg, 2011). at <http://link.springer.com/chapter/10.1007/978-3-642-21666-4_17>.
Coulter et al., Development and validation of a physical activity monitor for use on a wheelchair, Spinal Cord, 2011, vol. 49: pp. 445-450.
Gendle et al., Wheelchair-mounted accelerometers for measurement of physical activity. Disabil Rehabil Assist Technol., 2012, vol. 7: pp. 139-148.

(56) References Cited

OTHER PUBLICATIONS

Jang et al., Development of a wheelchair based body weight scale for people with disabilities. In Proceedings of the 4th International Convention on Rehabilitation Engineering & Assistive Technology 37:1-37:4 (Singapore Therapeutic, Assistive & Rehabilitative Technologies (START) Centre, 2010). at <http://dl.acm.org/citation.cfm?id=1926058.1926095>.

Chen et al., Obesity intervention in persons with spinal cord injury, Spinal Cord, 2006, vol. 44: pp. 82-91.

Taule et al. Factors influencing optimal seating pressure after spinal cord injury. Spinal Cord, 2013, vol. 51: pp. 273-277.

Yokota et al. The electric wheelchair controlled by human body motion interface: Classification of human body motion using Self-Organizing Map, 2010 IEEE International Conference on Industrial Technology (ICIT), 2010, pp. 1629-1634.

Giesbrecht et al., Measuring the effect of incremental angles of wheelchair tilt on interface pressure among individuals with spinal cord injury, Spinal Cord, 2011, vol. 49: pp. 827-831.

Sazonova et al., Accurate Prediction of Energy Expenditure Using a Shoe-Based Activity Monitor, Medicine & Science in Sports & Exercise, 2011, vol. 43: pp. 1312-1321.

Sazonova et al., Prediction of bodyweight and energy expenditure using point pressure and foot acceleration measurements, Open Biomed Eng J, 2011, vol. 5: pp. 110-115.

Sazonova et al., Monitoring of Posture Allocations and Activities by a Shoe-Based Wearable Sensor, Biomedical Engineering, IEEE Transactions, 2011, vol. 58: pp. 983-990.

Passing et al,. A new biometrical procedure for testing the equality of measurements from two different analytical methods, Application of linear regression procedures for method comparison studies in clinical chemistry, Part I, J. Clin. Chem. Clin. Biochem, 1983, vol. 21: pp. 709-720.

Zhang et al., Classification of posture and activities by using decision trees, 2012 Annual International Conference of the IEEE Engineering in Medicine and Biology Society (EMBC), 2012, pp. 4353-4356.

Zhang et al., Using Decision Trees to Measure Activities in People with Stroke, 2013 Annual International Conference of the IEEE Engineering in Medicine and Biology Society (EMBC), 2012.

Sazonov et al., Fuzzy logic expert system for automated damage detection from changes in strain energy mode shapes, Non-Destructive Testing and Evaluation, 2003, vol. 18: pp. 91-107.

* cited by examiner

PATIENT MONITORING SYSTEMS AND METHODS

CROSS REFERENCE TO RELATED APPLICATIONS

This non provisional patent application claims priority to U.S. Provisional Patent Application No. 62/010,199 entitled "Patient Monitoring Systems and Methods", filed Jun. 10, 2014, the content of which is herein incorporated by reference in its entirety.

BACKGROUND

Pressure ulcers, injuries to the skin and underlying tissues caused by prolonged pressure on the skin, are among the most common and costly secondary conditions after spinal cord injury (SCI). Pressure ulcers affect about 80% of individuals with SCI, with 30% of SCI patients developing multiple pressure ulcers. The annual cost of care is about $1.2 billion in the USA. In particular, the annual incidence rate ranges from 20-31% of SCI patients, and cost of care is estimated to be $40,000 per occurrence.

To aid in the prevention of pressure ulcers, pressure relief activities every 15-30 minutes have been recommended for persons with SCI. To minimize harmful pressure from sitting in a wheelchair, air-filled cushions are widely used by persons with SCI. Even if the person performs regular pressure relief activities, these cushions are typically ineffective in preventing ulcers if the cushions are over- or under-inflated. This is because people with SCI typically lack the sensation to detect when and where the cushion is "bottoming-out."

A number of different monitoring solutions have been attempted to address this issue, but they all suffer from shortcomings. Pressure-mapping systems measure the distribution of pressure on the interface between the cushion and the body. However, the high price (e.g., thousands of dollars) make such systems infeasible for widespread use. Currently used air pressure monitors are ineffective because air pressure changes with the applied load and does not reflect changes in weight distribution.

In addition, the SCI population is also at 2.5 times higher risk of obesity and overweight then those without the disability. Moreover, individuals who use a wheelchair have greater difficulty maintaining healthy weight because they have fundamental challenges in estimating physical activity and body weight. More strikingly, given the same BMI, persons with SCI usually carry a larger amount of fat than those without disabling conditions. Acutely, persons with SCI tend to lose weight because of the catastrophic injury and related hypermetabolism. After the acute phase, however, resting energy expenditure decreases with the loss of metabolically active muscle mass, and activity energy expenditure also decreases with a sedentary lifestyle. Without an appropriate dietary adjustment, energy intake can easily exceed daily energy requirements, leading to a weight gain. Maintaining healthy weight is complicated by the challenges in estimating physical activity and body weight in individuals who use a wheelchair. Physical activity monitoring solutions may range from wrist-worn accelerometers and multi-sensor body-worn systems to wheelchair-mounted systems. All body-worn sensors present an additional burden to the wearer and thus are not well suited for long-term use. Wheelchair-mounted device so far have been limited to tracking mobility of manually-propelled chairs rather than activity of the occupant. Similarly, attempts have been made to incorporate weight measurement capabilities into the wheelchair. However, such devices require physical modification of the wheelchair. Therefore, non-intrusive and accurate monitoring of physical activity and body weight of wheelchair users remains an open problem.

Therefore, a cost-effective monitoring program is needed to alleviate the burdens facing SCI survivors.

DETAILED DESCRIPTION

Various implementations of a patient monitoring assembly and methods of use are described herein. The patient monitoring assembly may be useful in preventing pressure ulcers, monitoring pressure relief regimen, physical activity, and managing body weight of a patient seated on the assembly. The patient monitoring assembly may be installed on a manual or powered wheelchair, for example, and continuously monitors and provides feedback to the patient and/or caregiver about whether the patient is engaging in pressure relief activities while seated on a cushion of the assembly, whether the patient's activities are in accordance with clinical guidelines for pressure relief, an estimate of the energy expended by the patient, and the weight and weight distribution of the patient seated on the assembly. The feedback may be provided in substantially real time via an audible or visual interface on the wheelchair and/or via a remotely located computing device, such as a smart phone.

Figure 1:
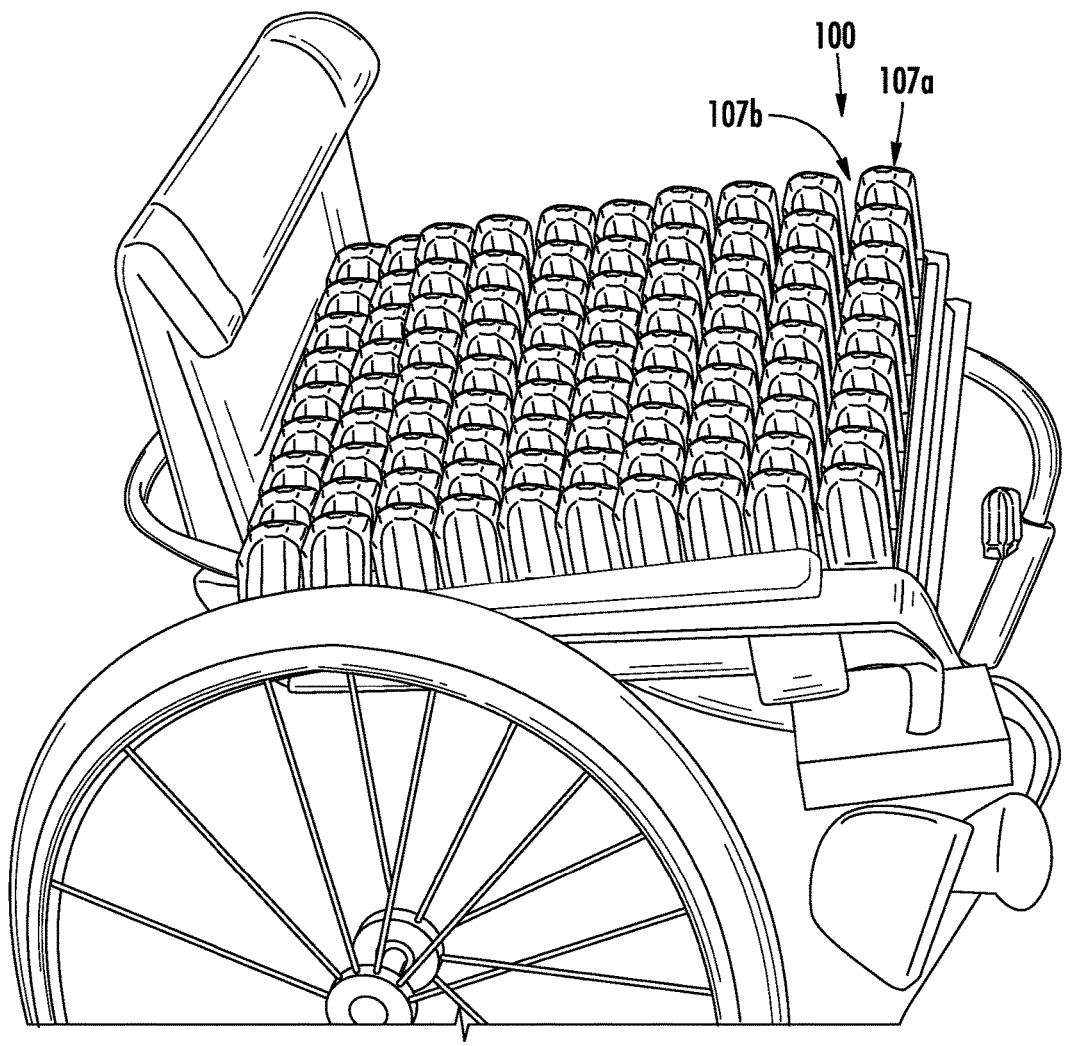
FIG. 1 illustrates a patient monitoring assembly installed onto a wheelchair, according to one implementation.
Figure 2:
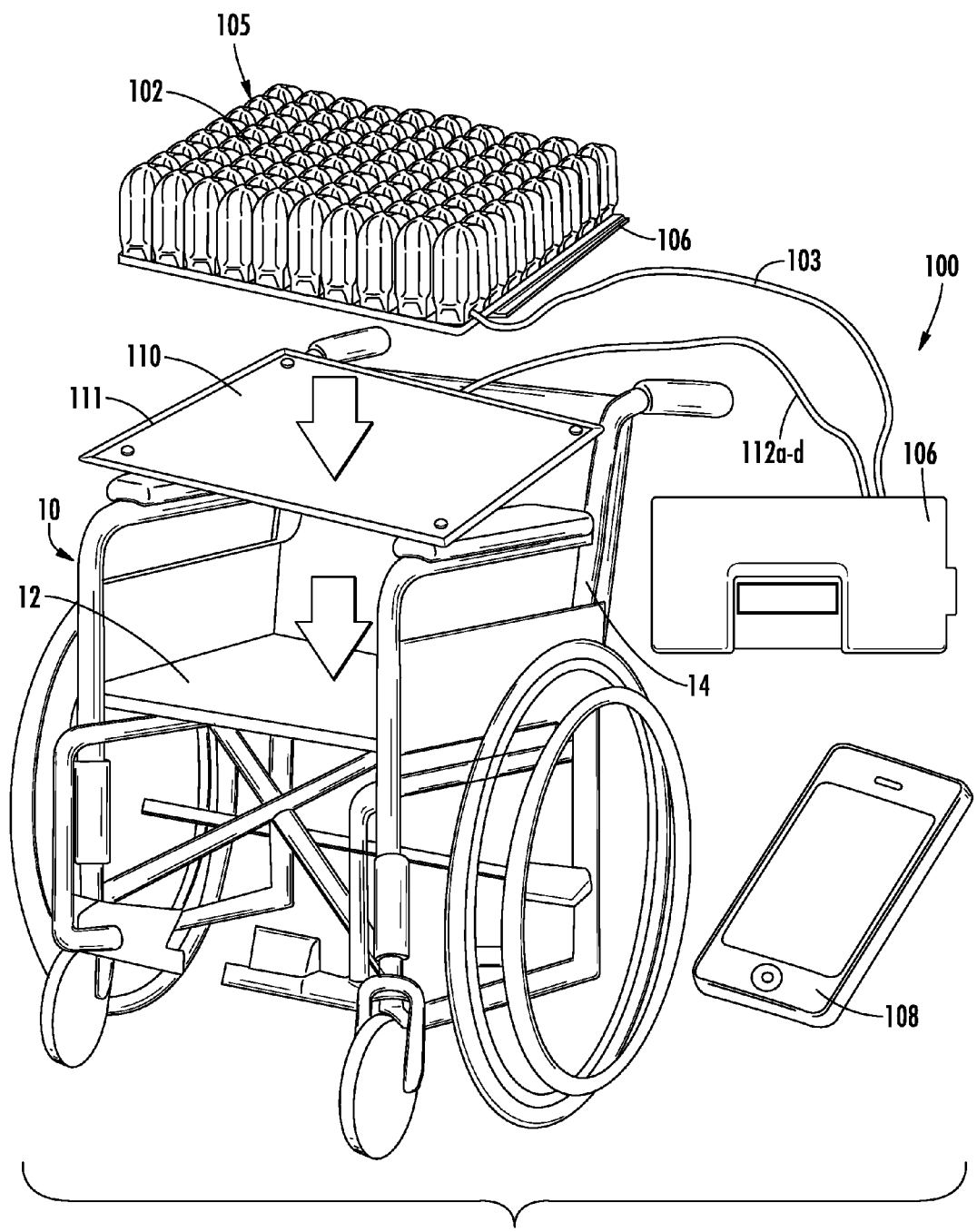
FIG. 2 illustrates an exploded view of the patient monitoring assembly shown in FIG. 1 installed on a seat cushion, according to one implementation.

FIGS. 1 and 2 illustrate a patient monitoring assembly system 100 according to one implementation that is installed on a wheelchair. The system 100 includes a support pad 110 that may be disposed on a seat support surface 12 of a wheelchair, a plurality of load cells attached to the support pad 110, a cushion 102 disposed on an upper surface 111 of the support pad 110, and an electronic control unit (ECU) 106 in electronic communication with the load cells. In addition, the ECU 106 is configured for wirelessly communicating with a remotely located computing device 108.

In the implementation shown, the cushion 102 is an air-filled cushion. To monitor proper inflation of the cushion 102, an air pressure conduit 103 is provided in sealed fluid communication between the cushion 102 and an air pressure sensor disposed outside of the cushion 102. The air pressure sensor is in electronic communication with the ECU 106. However, in other implementations in which the cushion 102 includes a non-air filled cushion, such as a gel-filled cushion, the air pressure conduit 103 and air pressure sensor would not be necessary.

The support pad 110 is made of a substantially rigid material, such as wood, plywood, rigid plastic, metal (e.g., steel or aluminum), or a plastic/metal composite material, and is about 0.25-0.75 inches thick (e.g., 0.5 inches thick in one implementation). The support pad 110 is generally planar and may be rectangular shaped. It has a lower surface 113 (shown in FIG. 3) that may be disposed on the seat support surface 12 of the wheelchair and an upper surface 111 opposite the lower surface 113 that faces upwardly when the pad 110 is disposed on the seat support surface 12.

Figure 3:
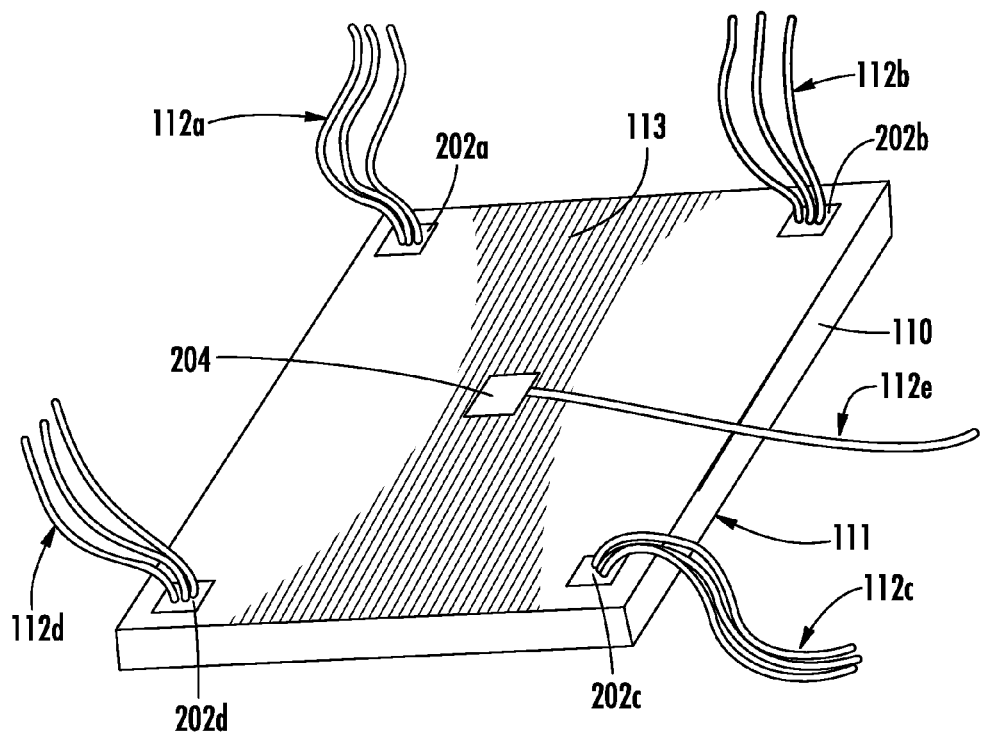
FIG. 3 illustrates an underside of the support pad 110 shown in FIG. 2 according to one implementation.

Four load cells 202a-202d are disposed on the underside 113 of the support pad 110 adjacent each of the four corners of the support pad 110, as shown in FIG. 3. In one implementation, the load cells 202a-202d are substantially equally spaced apart from each other. For example, the load cells 202a-202d may be disposed adjacent each corner of the support pad 110 or adjacent a center of each edge of the support pad 110. The cells 202a-202d may be integrated with the support pad 110 or attached using adhesives or mechanical mounting (e.g., screws, rivets, or specially shaped placeholders).

According to one implementation, the load cells 202a-202d may be based on the half-bridge strain gauges used in weighing applications. However, in other implementations, the load cells may be of any type that produces an electrical signal proportional to the applied force, such as capacitive, piezoresistive, hydraulic, or pneumatic load sensors. Each load cell has the range of about ¼ to about ½ of the full range of expected body weights, depending on the number of load cells used. The load cells allow for direct measurement of the load and load distribution. The load distribution is determined based on the known locations of each load cell.

Figure 4:
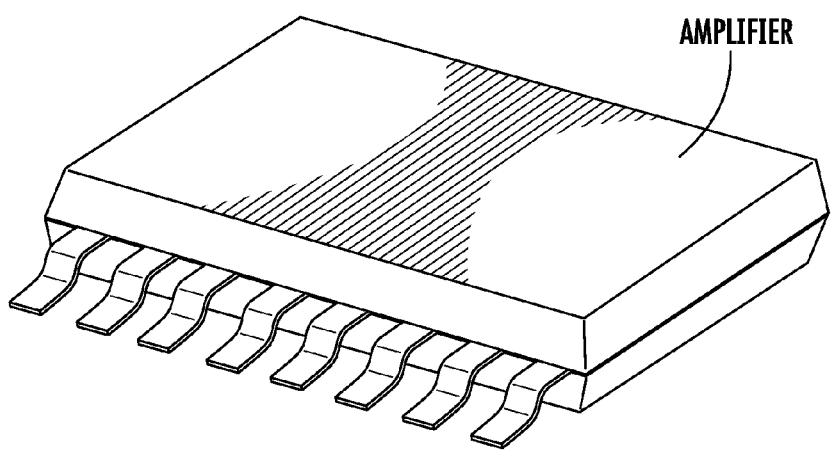
FIG. 4 illustrates a top view of an amplifier that may be used with force sensors according to one implementation.
Figure 6A:
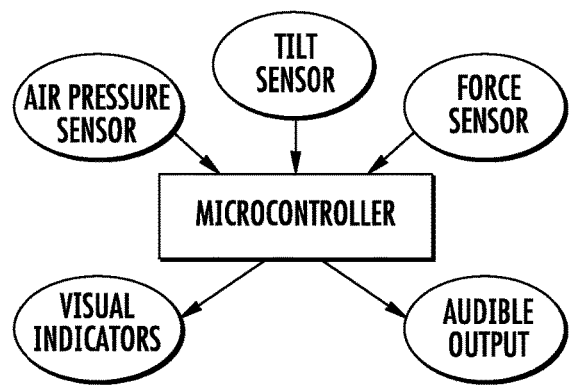
FIG. 6A illustrates a schematic of components in communication with a circuit board according to one implementation.
Figure 6B:
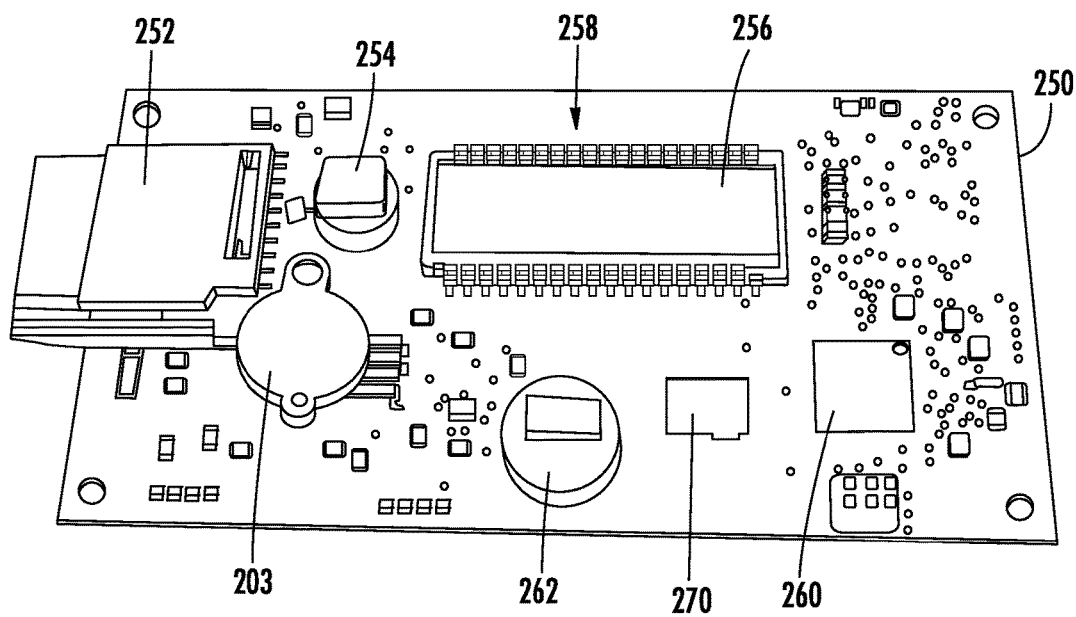
FIG. 6B illustrates a perspective view of a circuit board according to one implementation.
Figure 6C:
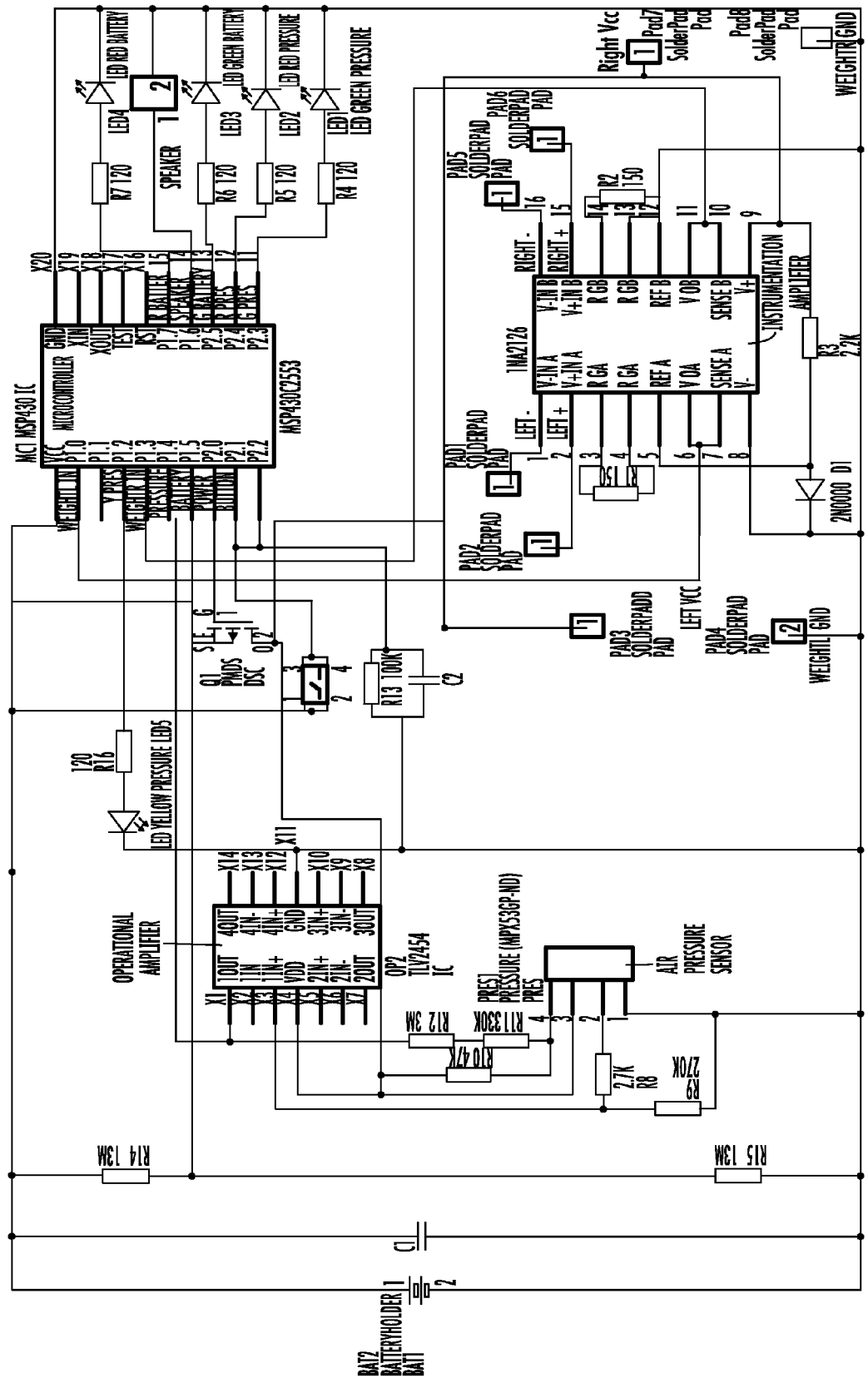
FIG. 6C illustrates a schematic of a circuit diagram for the instrumentation amplifier shown in FIG. 4, the air pressure sensor shown in FIG. 5, and the microcontroller shown on the circuit board in FIG. 6B, according to one implementation.

Sets of wires 112a-d extend from each load cell 202a-202d to the ECU 106, respectively. For example, in one implementation, three wires are associated with each load cell 202a-202d. The three wires include a ground wire, a power supply wire, and a signal wire. Each load cell 202a-202d is capable of performing measurements when powered by the power supply wire. When a load is applied to one or more load cells 202a-202d, a signal is sent from the load cell 202a-202d via the signal wire to an amplifier, such as a TI INA2126 dual sided operational amplifier shown in FIG. 4. The amplifier provides a gain of about 540, which is sufficient to provide readable signal levels to the microcontroller, which is described in more detail below in relation to FIG. 8. However, in other various implementations, the gain may be between about 0.1 to about 1000 as defined by the range of the output signal of the load cells. An exemplary circuit configuration for the amplified and load cells 202a-202d is shown in FIG. 6C. In addition, the load cells may be configured to communicate with the ECU 106 wirelessly if the load cells are provided with a power source for a wireless communication device (e.g., a Bluetooth device) for each load cell.

In one implementation, the signals from each load cell 202a-202d are individually processed, which allows the ECU 106 to determine whether there is movement by the patient in the anterior or posterior direction or the medial or lateral directions. This implementation also allows the ECU 106 to determine the body weight of the patient and the center of weight distribution on the cushion 102.

In another implementation, the load cells 202a-202d are paired together such that two load cells 202a, 202d are attached to one side of the amplifier and the other two load cells 202b, 202c are attached to the other side of the amplifier, as shown in the circuit diagram shown in FIG. 6C. On each side, one load cell is attached to a negative terminal to give a negative reading as a load is applied, and the other load cell is attached to a positive terminal to give a positive reading. Due to the differences in load cells, the reference pins for the amplifier may be attached to jumpers. This paired configuration allows the ECU 106 to detect movement in the medial or lateral directions (e.g., to the right or left side) relative to the patient seated above the pad 110 and allows for measurement of the body weight of the patient seated above the pad 110.

A tilt sensor 204, or three dimensional (3D) accelerometer may be optionally installed adjacent a central portion of the support pad 110 for measuring seat inclination, as shown in the implementation shown in FIG. 3. The tilt sensor 204 is particularly useful in implementations in which the patient monitoring assembly 10 is used on a motorized wheelchair for patients having higher degrees of SCI. However, in implementations in which the assembly 10 is to be installed onto manual or electric wheelchairs that cannot tilt backward, the tilt sensor 204 may not necessarily be included.

In the implementation shown in FIG. 3, the tilt sensor 204 is installed on the underside 113 of the support pad 110 and is centrally disposed relative to the load sensors 202a-202d and the underside 113 of the support pad 110. For example, in one implementation, the tilt sensor 204 may be an ADXL 337 from Analog Devices, Inc. In general, other implementations may include any sensor that can provide a signal proportional to the sensor's orientation in the field of Earth's gravity can serve as the tilt sensor 204, including multiple commercially available analog and digital tilt sensors and acceleration sensors. The tilt sensor may be mounted on any side of the support pad by adhesives or mechanical mounting solutions.

The tilt sensor 204 detects the angle of inclination of the support pad 110. For example, clinical guidelines may suggest that pressure relief is provided by inclination of the seating surface at an angle greater than about 30° for a certain period of time. As an example, the seat of a motorized wheelchair may be tilted as much as 65° to provide pressure relief and the relief activity can last as long as about 1 to about 4 minutes. Wire(s) 112e extend from the tilt sensor 204 to the ECU 106. The analog or digital signal from the tilt sensor 204 carries information about seat inclination to the ECU 106.

As mentioned above, the cushion 102 may include an air cushion, such as the air cushion shown in FIGS. 1 and 2. The air cushion 102 shown in this implementation includes an upper surface 105 and a lower surface 106, and the upper 105 and lower surfaces 106 define at least one chamber there between for holding air. The lower surface 106 is disposed on the upper surface 111 of the support pad 110, and the upper surface 105 of the air cushion 102 faces generally upwardly away from the support pad 110. The patient may sit on the upper surface 105 or on a cover (not shown) disposed over the upper surface 105, for example. The upper surface 105 defines an array of peaks 107a and valleys 107b, which form an egg-crate like surface. The interior portions of the peaks 107a are in fluid communication with the chamber.

Figure 5:
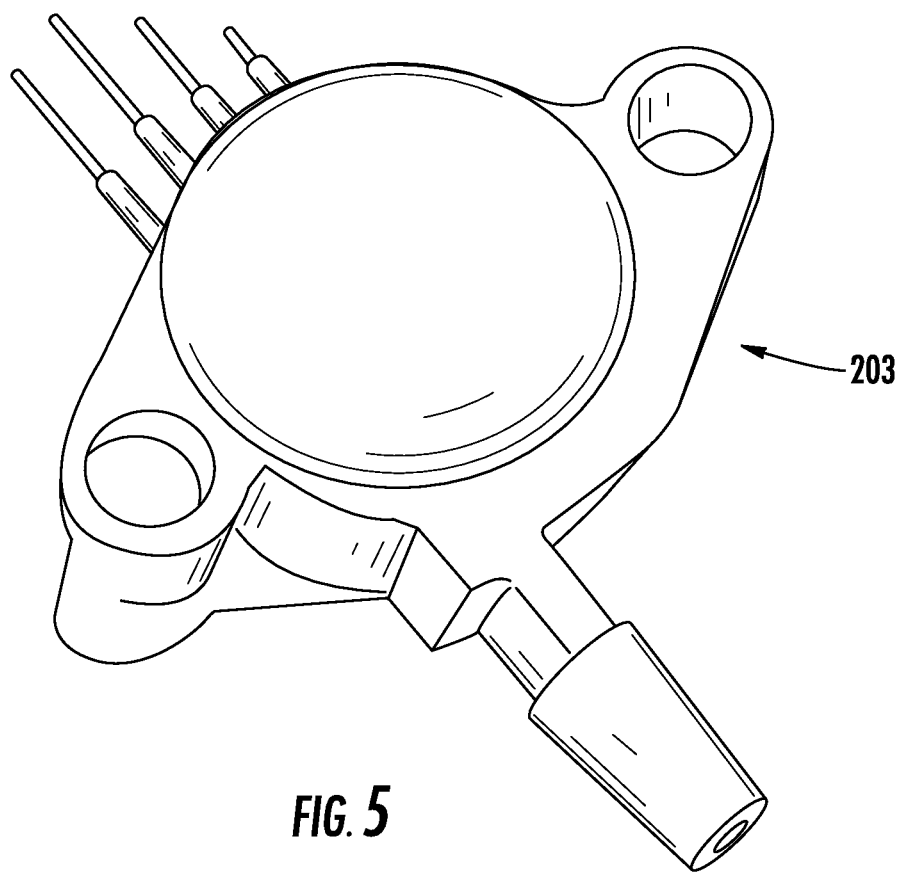
FIG. 5 illustrates a top view of an air pressure sensor according to one implementation.

At least one air conduit 103 is securely installed to be in fluid communication with each chamber and an air pressure sensor disposed outside of the air cushion 102. The air pressure sensor detects the air pressure in the chamber. The air pressure within the air cushion 102 may be up to about 7.25 pounds per square inch (psi), with the actual pressure depending on the size, body weight of the user and the type of the air cushion used. FIG. 5 illustrates an exemplary air pressure sensor 203 that may be used with the patient monitoring assembly 100, and FIG. 6C illustrates an exemplary circuit schematic for the air pressure sensor 203. The air pressure sensor 203 shown is a Freescale Semiconductor MPX53GP gauge type pressure sensor. However, other suitable analog and digital air pressure sensors may be used with the assembly 100 in other implementations. Suitable sensors have a measurement range that exceeds the highest pressure expected from the cushion and resolution sufficient to differentiate between the degrees of cushion inflation.

As mentioned above, in other implementations, the cushion on the support pad 110 may include a gel-filled cushion or a cushion filled with another suitable substance other than air. In such an implementation, the air conduit 103 and air pressure sensor 203 are not necessarily included in the system 10 since air pressure monitoring may not be required.

The ECU 106 is configured for receiving the signals from the load cells 202a-202d, tilt sensor 204, and air pressure sensor 203 to monitor and evaluate movement of the patient sitting on the assembly 100 and to ensure proper operation of the assembly 100. The ECU 106 comprises a circuit board, such as the circuit board 250 shown in FIG. 6B. The circuit board 250 includes a storage card 252, a depressible button 254, an alpha-numeric liquid crystal display (LCD) screen 256, a plurality of light emitting diodes (LEDs) 258 disposed adjacent the LCD 256, a microcontroller 260 associated with the load cells 202a-202d and the tilt sensor 204, an audible buzzer alarm 262, and an air pressure sensor 203 in fluid communication with the air conduit 103 extending from the air cushion 102. The ECU 106 may also include a Bluetooth wireless communication device 270 for sending signals from the ECU 106 to a remotely located computing device via Bluetooth wireless communication.

The components on the circuit board 250, the load cells 202a-202d, the tilt sensor 204, and the Bluetooth device 270 may receive power from the battery used by the wheelchair if the wheelchair is an electric wheelchair or from a battery that is part of the patient monitoring assembly 100. Power is periodically supplied to the air pressure sensor 203, the load cells 202a-202d, and the tilt sensor 204 with the period being between about 10 milliseconds to about 30 seconds. If the processor of the ECU 106 senses that the patient is not in the seat, the ECU 106 provides power to the various sensors less frequently to save power. For example, the processor may sense absence of the patient in the seat if the force signals indicate that the weight on the seat is less than about 20% of an expected weight when the patient is in the seat. In response to sensing that the patient is out of the seat, the processor may indicate to the ECU 106 to provide power to the sensors every about 30 seconds until the force signals indicate that the weight on the seat is at least about 80% of the expected weight. The expected weight may be calibrated for the patient during the patient's first use of the wheelchair or at a later time.

When the processor determines that the patient is in the seat, the period with which power is supplied to the sensors varies by application and the posture allocation assumed by the patient in the wheelchair. For example, when monitoring for air cushion inflation, the sensors may be read every 30 s. Once a potential cushion deflation is detected, the subsequent readings may be taken every about 1 to about 5 seconds to monitor the situation on a shorter time scale. As another example, when monitoring physical activity, the load cell sensors may be read as frequently as every about 10 milliseconds to capture the variation in sensor signals due to body motion. The specific power management scheme for powering the sensors is defined by which of the monitoring modes are active at a given moment of time: for example, cushion inflation (e.g., about 1 to about 30 seconds), pressure relief (e.g., about 10 milliseconds to about 30 seconds), physical activity monitoring (e.g., about 10 milliseconds to about 30 seconds), and body weight measurement (e.g., about 10 milliseconds to about 30 seconds).

Figure 7:
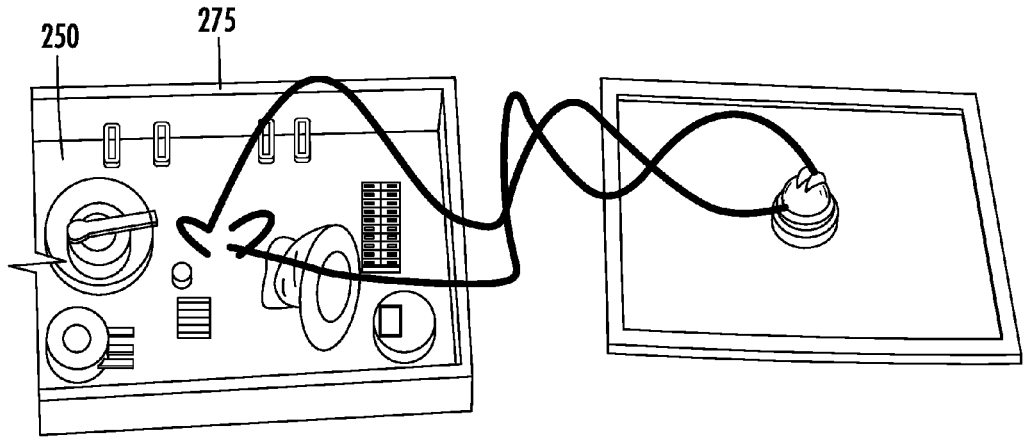
FIG. 7 illustrates a perspective view of an enclosure with the printed circuit board shown in FIG. 6B, according to one implementation.

FIG. 7 illustrates the circuit board 250 installed in an enclosure 275 to protect the components thereof. The enclosure may be made of a plastic material or any other suitable materials for enclosing the circuit board.

In another implementation (not shown), the electronics of the system may be fully integrated into the support pad containing the load cells, and an external wirelessly connected computing device may act as the user interface.

Figure 8:
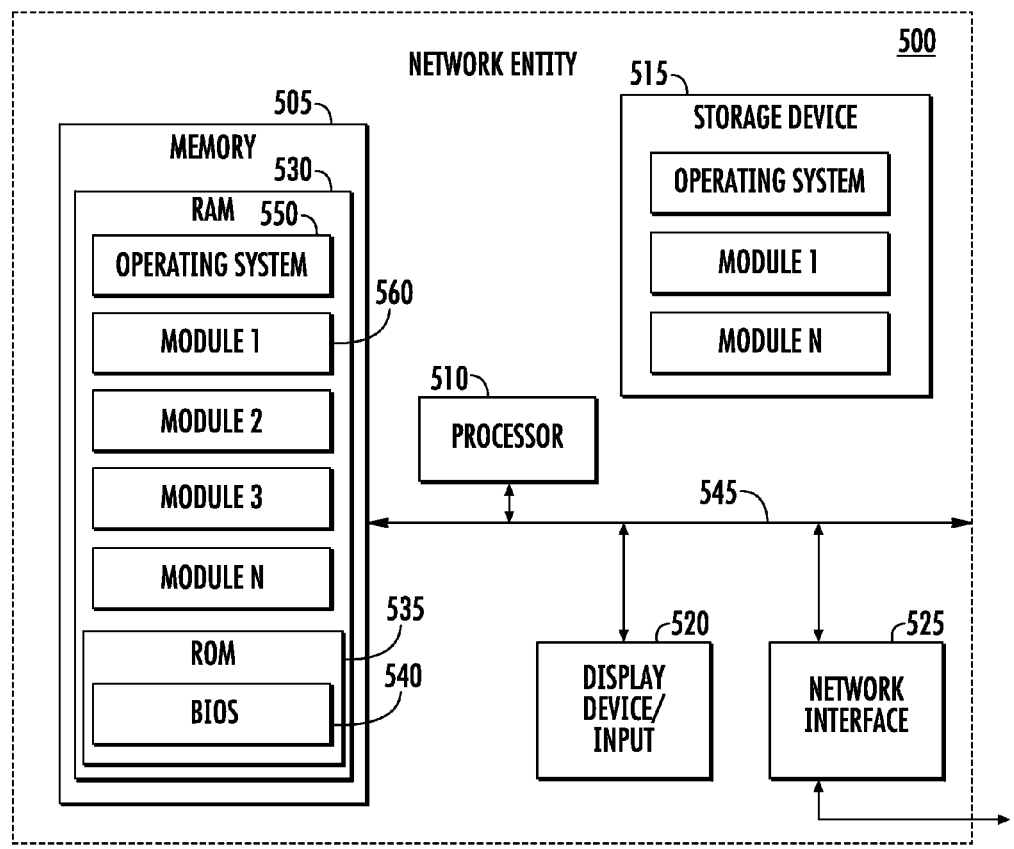
FIG. 8 illustrates a schematic diagram of a computer system according to one implementation.

FIG. 8 illustrates a schematic of a central server 500, or other similar network entity, configured to implement a computer system, according to one implementation. The server 500 executes various functions of the system 100 described above in relation to FIGS. 1 through 7. For example, the server 500 may be the ECU 106 described above, or a part thereof. As used herein, the designation "central" merely serves to describe the common functionality the server provides for multiple clients or other computing devices and does not require or infer any centralized positioning of the server relative to other computing devices. As may be understood from FIG. 8, the central server 500 may include a processor 510 that communicates with other elements within the central server 500 via a system interface or bus 545. The processor 510 may include the microcontroller 260 described above in relation to FIGS. 6A-6C. Also included in the central server 500 may be a display device/input device 520 for receiving and displaying data, including signals from the various sensors. This display device/input device 520 may be, for example, a keyboard or pointing device that is used in combination with a monitor. The central server 500 may further include memory 505, which may include both read only memory (ROM) 535 and random access memory (RAM) 530. The server's ROM 535 may be used to store a basic input/output system 540 (BIOS), containing the basic routines that help to transfer information across the one or more networks.

In addition, the central server 500 may include at least one storage device 515, such as a secure digital (SD) storage card, a hard disk drive, a floppy disk drive, a CD Rom drive, or optical disk drive, for storing information on various computer-readable media, such as a hard disk, a removable magnetic disk, or a CD-ROM disk. As will be appreciated by one of ordinary skill in the art, each of these storage devices 515 may be connected to the system bus 545 by an appropriate interface. The storage devices 515 and their associated computer-readable media may provide nonvolatile storage for a central server. It is important to note that the computer-readable media described above could be replaced by any other type of computer-readable media known in the art. Such media include, for example, magnetic cassettes, flash memory cards and digital video disks.

A number of program modules may be stored by the various storage devices and within RAM 530. Such program modules may include an operating system 550 and a plurality of one or more (N) modules 560. The modules 560 may control certain aspects of the operation of the central server 500, with the assistance of the processor 510 and the operating system 550. For example, the modules may perform the functions described above in relation to FIGS. 1 through 6B and illustrated by the figures and other materials disclosed herein, such as executing various functions of the monitoring system 10. According to various implementations, one or more of the modules may be executed by a digital computing system or portion thereof, such as a microcomputer, digital signal processor chip, field programmable gate array (FPGA) system, PC, or other suitable computing device.

In one exemplary implementation, the server 500 includes the following modules: (1) a pressure relief detection module for using signals received from the force sensors, tilt sensor, and/or air pressure sensor to identify one or more pressure relieving movements being performed and a duration and/or number of times that each movement is performed; (2) a physical activity detection module for using signals received from the force sensors, tilt sensor, and/or air pressure sensor to identify (or estimate) a level of physical activity (e.g., an intensity, such as light or vigorous), type of activity (e.g., a certain exercise), and/or amount energy (e.g., calories) expended; (3) a feedback module for providing feedback about the number of times and/or a duration for which each pressure relieving movement is performed based on clinical guidelines for each pressure relieving movement, providing feedback about the physical activity of the patient over a certain time period (e.g., a day, a few hours) based on movements sensed by the force, tilt, and/or air pressure sensors, and generating messages for the patient and/or caregiver indicating compliance with each guideline, prompting the patient to perform a particular pressure relieving movement or exercise, and/or indicating an amount of energy expended over the certain time period; (4) a dangerous condition module for comparing force signals and/or air pressure signals with signals indicating one or more dangerous conditions and in response to the signals being indicative of one or more dangerous conditions, generating a message indicating the occurrence of the dangerous condition; (5) a calibration module for receiving calibrated air pressure signals from the air pressure sensor and calibrated load signals from the load cells indicating a preferred air pressure in the air cushion, an initial weight of the patient, and an acceptable weight distribution of the patient over the support pad; and (6) an communication module for communicating generated messages to the user and/or caregiver via audible, visual, and/or haptic messages delivered proximate to the wheelchair and/or to a remotely located computing device.

The system receives signals from the load cells 202a-202d, air pressure sensor 203, and tilt sensor 204 periodically. For example, the frequency at which the signals are read may be about 30 times per second to about 1 time per 30 seconds. And, the signals for one sensor may be read more or less frequently that the signals from another sensor, as noted above.

As mentioned above, the pressure relief detection module compares signals received from the force sensors, tilt sensor, and/or air pressure sensor with ranges of signals associated with each respective sensor that indicate the performance of a pressure relieving movement. Pressure relieving movements may include leaning forward, leaning right, leaning left, tricep push ups, or backward tilting, for example. Based on the results of this comparison, the activity detection module identifies whether and which of the pressure relieving movement is being performed by the patient. In one implementation, the identity of the movement is stored in the memory along with a duration for each identified movement. Movements qualifying as pressure relieving movements, the number of times each movement should be performed in a certain time period (e.g., a day, an hour, a few hours) and the duration for performing each movement (e.g., about 1 to about 3 minutes) may be set by clinical guidelines and incorporated into the system.

In particular, according to one implementation, the pressure relief detection module may use feature computation to extract information of interest from the signals received from the force sensors, tilt sensor, and/or air pressure sensor signal. Such features may include mean, standard deviation, entropy, variance, maximum value, number of mean crossings, and mean absolute deviation. To save power and minimize the amount of computation, forward feature selection may be used to identify the most relevant features to be computed. For example, the difference between the mean load sensor reading on the left side versus the mean lead sensor reading on the right side may indicate that the patient in chair is leaning to the left side or the right, which are pressure relief movements. Similarly, the difference between the mean load sensor reading on the front side versus the mean load sensor reading on the back side may indicate that the patient is leaning forward. In addition, mean load sensor readings on all of the load cell sensors indicating repeated fluctuations in force that are consistent among the load cell sensors may indicate tricep push ups.

In one implementation, the pressure relief detection module may use a low-power pattern recognition algorithm (e.g., decision tree) to identify the signals that indicate each pressure relief movement. The decision tree algorithm is a class of machine learning algorithms that learns or trains from examples of given situation. For example, the training data used to "teach" the algorithm may be collected by a small pilot study of 2 to 3 able bodied persons, for example. After establishing base line pattern ranges with this initial data, the algorithm may then continue to learn from data collected from additional able bodied participants. An exemplary method of how this algorithm is "taught" is described below in the section entitled "Validation Study of Exemplary Patient Monitoring System." However, other means of collecting the data used to teach the algorithm are possible and within the scope of the invention. In addition, other types of learning networks may be used to identify the pressure relief movements, such as neural networks, Bayesian networks, or other suitable learning algorithms. Furthermore, the data indicating parameters for each pressure relief movement or levels of physical activity may be predetermined and input into the system prior to patient use of the system or thereafter.

One or more of the following class labels may be applied to every 30 seconds (or other period of time) of sensor data: (1) normal sitting, (2) leaning forward, (3) backward tilt, (4) leaning left, (5) leaning right, (6) triceps push up, or (7) chair unoccupied. Pressure relieving movements may include tilting backwards, leaning left or right, and pushing up with the triceps. Thus, the pressure relief detection module identifies which of these movements is being performed based on the signals received and may store this information for use by other modules or for communicating to the patient and/or caregiver.

Similar to the pressure relief detection module, the physical activity detection module uses signals received from the force sensors, tilt sensor, and/or air pressure sensor to identify (or estimate) a level of physical activity (e.g., an intensity, such as light or vigorous), type of activity (e.g., a certain exercise), and/or amount energy (e.g., calories) expended. For example, physical activity estimates may be based on an assumption that any body movement of the patient results in minute variations in load cell signals (and, optionally, air pressure signals when an air cushion is used with the system). However, in this system, an average of normalized signals from the load cells, and optionally, signals from the air pressure sensor, may be used to estimate the magnitude of body motion. In addition, the normalized signals from the load cells may be used to estimate caloric energy expenditures without having to attach a separate device to the patient. In one example, the average normalized signals are computed for about 30 seconds of data.

The feedback module may be configured to provide feedback about the number of times and/or a duration for which each pressure relieving movement is performed based on clinical guidelines for each pressure relieving movement, estimate and provide feedback about an amount of energy expended by the patient over a certain time period (e.g., a day, a few hours), and generate messages for the patient and/or caregiver indicating compliance with each guideline and/or prompting the patient to perform a particular pressure relieving movement. For example, the feedback module may be configured to compare the number of times each pressure relieving movement is performed and/or an elapsed time that each pressure relieving movement is performed with clinical guidelines for each pressure relieving movement. For example, estimation of the sufficiency of the pressure relief activities may include using the following metrics: (1) number and duration of pressure relief episodes in a particular time period (e.g., a day, the past hour, past 30 minutes, past 15 minutes), (2) relative load reduction for backward tilt and push-ups, and (3) chair inclination for backward tilt. These metrics may be used with empirically formulated "if-then" statements (e.g., fuzzy logic rules) that follow clinical guidelines to evaluate the sufficiency of the pressure relief movement.

The feedback module may also be configured for estimating body weight using statistical methods to produce accurate measures from the multiple sensor readings accumulated over a period of time. For example, first, episodes of "quiet sitting" may be detected by the algorithms described above (e.g., all 30 second intervals of activity labeled as normal sitting and physical activity measure is below a threshold). Second, multiple estimates of body weight are computed from each 30 second episode of quiet sitting as a linear regression of mean values from each of the load cells. Third, statistical outlier detection is applied to reject extreme values and produce an estimate of body weight. Because part of the patient's body may be supported by leg rests when seated in a wheelchair, a certain error may be introduced into the estimate. However, for a given patient, this error may be constant and can be compensated for through calibration.

The message generated by the feedback module may communicated by the communication via audible, visual, or haptic means. For example, the audible message may include an instruction for the communication module to activate a buzzer or alarm or generate a spoken message using computer-generated language. The visual message may include an instruction for the communication module to display an alpha-numeric message or activate a certain LED or group of LEDs. For example, the visual message may include an instruction to activate a red LED if no pressure relieving activities have been performed for a given time period, a yellow LED if some pressure relieving activities have been performed but the amount still falls short of the goal, or a green LED if a sufficient amount of pressure relieving activities have been performed. As a specific example, the instruction may be "if number_of_episodes_1 hr>10 then pressure_relief=green." The fuzzy estimate of pressure relief sufficiency may be derived from multiple rules and presented on a color scale using the LEDs on the circuit board. The visual message may also be communicated via Bluetooth or other wireless network to a remotely located computing device, such as a smart phone or stand alone computing device, for display thereon. The haptic message, which may include a vibration or other sensory message, may be communicated by a haptic device disposed on the wheelchair, the circuit board, or on the remotely located computing device.

The dangerous condition module may be configured for identifying a dangerous condition, such as over inflation of the air cushion, under inflation of the air cushion, lack of performing pressure relief movements or insufficient performance of the pressure relieving movements, uneven weight distribution over the support pad for a prolonged time period (e.g., leaning to a side or forward), excessive leaning to a side or forward (e.g., putting too much weight on one side or forward that may lead to the air cushion "bottoming out"), and low voltage in the internal battery or wheelchair battery. In particular, the dangerous condition module uses the air pressure signal, force signals, and/or tilt signal to identify one or more dangerous conditions. In response to the signals indicating one or more dangerous conditions, the dangerous condition module generates a message indicating the identity of the dangerous condition. For example, the dangerous condition module may use feature selection computation, which is described above in relation to the activity detection module, to identify the one or more dangerous conditions. The dangerous condition may be detected by comparing the received signals with calibrated signals acquired by the calibration module (discussed below) and identifying a dangerous condition when the received signals are outside of a certain range of the calibrated signals. And, certain dangerous conditions may be identified if the received signal(s) are outside of a certain range of the calibrated signals for more than a predetermined time period. For example, a dangerous condition may be identified when the received air pressure signal is outside of about 20% of the calibrated air pressure for more than one minute or immediately if the air pressure is outside of about 50% of the calibrated air pressure. Clinical guidelines may provide guidance as to how to define dangerous conditions and what sensor data may be useful in identifying them.

The feedback generated by the feedback module in response to receiving an identification of a dangerous condition from the dangerous condition module may be similar to the type of audible, visual, and/or haptic feedback described above. For example, the feedback module may instruct the communication module to flash the yellow LED when the battery voltage for the battery internal to the patient monitoring system is below a first threshold voltage and flash the red LED when the battery voltage is below a second threshold voltage that is lower than the first. As another example, the feedback module may instruct the communication module to display at message on the LCD that indicates the air pressure is low, such as "AIR LOW".

Furthermore, the feedback module may provide a set of historical sensor data to the remotely located computing device. This information could be useful for the physical therapist or caregiver in assessing the sufficiency of physical movement for the patient, what pressure relieving movements are performed, how often are they performed, and how well are they working for the patient, monitoring weight gain/loss trends over time for the patient, and the frequency of dangerous conditions.

The calibration module receives the patient's weight, normal weight distribution, and preferred or optimal air pressure in the cushion upon initial use of the patient monitoring system and saves the calibrated weight, weight distribution, and air pressure to the memory. For example, these calibrated values may be received by the calibration module via a user interface of the ECU 106. Upon power up of the wheelchair monitoring system thereafter, the calibrated values are loaded from the memory and used by the processor for various monitoring functions. The calibration of one or more of these values may occur after the initial use of the wheelchair monitoring system by the patient if certain conditions suggest the need for an updated calibration, such as if the patient gains or losses a certain amount of weight. Possible methods of calibrating these values are described in the section below entitled "Description of Validation Study of Exemplary Patient Monitoring System."

The communication module is configured for communicating the generated messages to the user and/or caregiver via audible, visual, and/or haptic messages delivered proximate to the wheelchair and/or to a remotely located computing device, such as is described above in relation to the feedback module.

Description of Validation Study of Exemplary Patient Monitoring System

To validate the efficacy and operation of the patient monitoring system, the applicants intend to study use of the patient monitoring system by about 20 able-bodied (AB) adult individuals prior testing on the system with individuals that lack pressure sensation. The accuracy of the patient monitoring system will be quantitatively assessed and additional data will be collected for calibration of the pattern recognition algorithms described above.

The adults to be studied initially will include a range of males and females, lean, overweight and obese individuals (e.g., BMI 18-45) so that operation of patient monitoring system is tested on individuals of having varying anthropometric characteristics. Inclusion criteria will include adults with BMI in the range of 18-45. Exclusion criteria will include adults with a self-reported lack of pressure sensation in the lower body. Half of the group will be assigned to a manual wheelchair (MW) group using a low-profile air cushion (e.g., ROHO LOW PROFILE® 2.5" Dual Valve Cushion), and the other half will be assigned to an electric wheelchair (EW) group using a high-profile cushion (e.g., ROHO HIGH PROFILE® 4" Dual Valve Air Cushion). These conditions will emulate typical solutions for individuals with paraplegia and tetraplegia.

The patient monitoring system will be tested in the laboratory to validate detection of hazards that may lead to initiation of pressure ulcers. Each participant will report to a particular laboratory, and the optimal air pressure for that participant will be calibrated using a pressure mapping system (e.g., ROHO XSensor®). In addition, body weight and height measurements will be taken, and participants will be trained to use the wheel chair and patient monitoring system. Each subject will be asked to sit comfortably in wheelchair for 6 hours (e.g., three 2-hour episodes separated by breaks) while reading a book, watching movies or working on a computer. At random times the participants will be prompted to simulate a hazardous condition (for example, lean and remain leaning to one side for 5 minutes or until they experience a discomfort). A total of 18 (once per half hour) hazardous conditions will be tested. The participants will also be prompted to perform regular pressure relief activities (18 times total).

Second, the patient monitoring system will be tested on the same individuals using a manual or powered wheelchair in the community for a period of 3 days. The participants will be using the wheelchair for the duration of a waking day in the same manner as SCI individuals (with legs strapped to leg rests of the chair, body motion restricted using seat belts, etc.), performing the same pressure relief activities as individuals with SCI, and following alerts/messages from patient monitoring system if necessary. For example, the alerts and prompts to perform pressure relief movements may be communicated to each participant via the LCD and/or LED on the circuit board of the patient monitoring system and/or through an application running on the participant's smartphone. In addition, the participant will be asked to mark every alert as true or false or to report non-detected events through the application running on the participant's smartphone. Alternatively, the participant may enter this information via another type of computing device, such as desktop or laptop computer.

During community testing, the participants will also wear a wrist calorimeter (e.g., a SenseWear calorimeter that relies on heat flow for energy expenditure measurement) to estimate energy expenditure. Another direct or indirect calorimetry device, a room calorimeter, or an accurate physical activity monitor can be used for calibration. The participants will also be asked to take a body weight measurement on a floor scale (e.g., Tanita® HD-351BT Bluetooth Wireless Digital Weight Scale) in the beginning and end of every day. In all experiments, the sensor data from patient monitoring system will be logged in the memory (e.g., the SD card on the circuit board) for further analysis. Signals from the wrist-worn accelerometer will be stored on the internal memory of the accelerometer device, and body weight measurements from the floor scale will be automatically logged by the smartphone or other computing device associated with the participant.

The accuracy of the event detection (both hazardous conditions and pressure relief activities) will be evaluated by using counts of true positives (TP), false positives (FP) and false negatives (FN). These counts will be obtained by matching observations in the laboratory study and self-report through the smartphone application (or data entered via other computing devices) in the community study with events detected by patient monitoring system. The reliability of events detection will be expressed as F-measure $F_1=(2*TP)/(2*TP+FN+FP)$, wherein TP is the number of true positives, FN is the number of false negatives, and FP is the number of false positives. The proposed measure is well-suited for datasets dominated by true negatives, such as the dataset being evaluated.

Body weight estimates (PMSBW) will be evaluated with respect to floor scale measurements (FSBW). Measurements taken by the floor scale will be paired with patient monitoring system measurements taken approximately at the same time. A paired two-sided t-test with null hypothesis H0: $\mu_{PMSBW}=\mu_{FSBW}$ and H1: $\mu_{PMSBW}\neq\mu_{FSBW}$, wherein $\mu_{PMSBW}$ is the mean value for body weight calculated by the patient monitoring system and $\mu_{FSBW}$ is the mean value for the body weight calculated by the floor scale, will test the significance of the accuracy of the body weight estimates. The power of such test can be estimated in terms of the effect size (mean difference over standard deviation of the difference): for the sample size of 10 participants who will provide at least 6 measurements each during the course of the study, the effect size of 0.37 can be detected with 80% power and effect size of 0.43 with 90% power.

The correlation of activity measures from the direct calorimeter ($SW_{PA}$) and physical activity measures computed from the patient monitoring sensors ($WCM_{PA}$) will be evaluated using Pearson's correlation coefficient computed for each day of observation $$r = \frac{\sum_{i=1}^{n}(SW_{PA}^i - \overline{SW_{PA}})(WCM_{PA}^i - \overline{WCM_{PA}})}{\sqrt{\sum_{i=1}^{n}(SW_{PA}^i - \overline{SW_{PA}})^2}\sqrt{\sum_{i=1}^{n}(WCM_{PA}^i - \overline{WCM_{PA}})^2}}.$$

It is expected that the $SW_{PA}$ will be highly correlated to $WCM_{PA}$ (e.g., r≈0.7-0.9). For correlation coefficient 0.8 and sample size of 30 (10 participants in each group times 3 days of observation), the power of the test will be above 0.99.

The difference in accuracy of event detection (F-measure), body weight estimates $PMS_{BW}$, and physical activity estimates $WCM_{PA}$ between the manual wheelchair and electric wheelchair groups will be evaluated by a two-sample one-sided t-test to show that the metrics are not significantly different between the two groups. Thus, the hypotheses to be tested are for H0: $\mu_{F_{MW}} = \mu_{F_{EW}}$ against H1: $\mu_{F_{MW}} < \mu_{F_{EW}}$. Absolute error of body weight measurement $e_{BW}^i = |WCM_{BW}^i - BW^i|$ will be tested for $H_0$: $\mu_{e_{MW}}$ against $H_1$: $\mu_{e_{MW}} < \mu_{e_{EW}}$. The physical activity measures will be tested for $H_0$: $\mu_{r_{MW}} = \mu_{r_{EW}}$ against $H_o$: $\mu_{r_{MW}} < \mu_{r_{EW}}$. Given that the minimum sample size in any of these tests will be 30, each test will provide at least 80% power to detect effect size of 0.65 and at least 90% power to detect effect size of 0.76.

Finally, the analysis of the accuracy for each method with respect to the BMI will be performed using a Passing-Bablok orthogonal regression, which will result in an equation of the form Y=a+bX, wherein Y is a given method's measure of error (F1, $e_{BW}^i$ or r) and X is the BMI. A significant difference of the intercept from 0 indicates the fixed bias and the significant difference of the slope from zero indicates the proportional bias.

Then, to validate the patient monitoring system with patients with SCI, about 20 adults (e.g., over 19 years old) that are paraplegia or quadriplegia or tetraplegia due to a spinal cord injury will be asked to participate. SCI patients that are not currently using a wheelchair with an air cushion will not participate. Ten individuals with paraplegia will be tested first, followed by 10 individuals with a higher degree of injury (e.g., tetraplegia).

The optimal air pressure for each participant will be calibrated using a pressure mapping system (e.g., ROHO XSensor®) at the laboratory, and participants will be trained in how to use the patient monitoring system.

Next, the patient monitoring system will be tested on the same SCI individuals for a period of 7 days. The participants will be using the patient monitoring system and following alerts/messages from patient monitoring system if necessary. Unlike the study with the able-bodied individuals, participants the SCI community study will not have to mark every detected event as true or false. Instead, the perceived accuracy of the event detection will be evaluated using a questionnaire after the study. The participants will wear a wrist accelerometer (e.g., GT3X+ Monitor from ActiGraph, SenseWear or other device) to estimate physical activity. Other direct or indirect methods (e.g. room calorimeters or doubly labeled water) may be used. The body weight measurements will be taken by the wheelchair scale available at the laboratory at the beginning and end of the study.

Most of the analysis and power considerations described above are directly applicable to the analysis with the SCI participants and will be applied in the exactly the same manner.

In addition, the study with the SCI participants will establish qualitative (as perceived by the participants) measures of the patient monitoring system comfort and usefulness of feedback (including reliability of alerts). Upon completion of the SCI participant study, the participants will fill out questionnaires assessing comfort of using the patient monitoring system (e.g., based on Knight and Baber assessment) and self-perceived behavioral impact of the patient monitoring system feedback based on post-then-pre test design.

CONCLUSION

Although the above figures and description describe the use of the patient monitoring system for use with a wheelchair, the system may be adapted for use in beds, chairs, and other support surfaces. In addition, the above description and claims refer to comparing the received signals from various sensors to expected signals indicating various conditions or pressure relieving movements, for example. However, it should be understood that this term should be interpreted to include the signals, transformations of the signals, or values derived from the signals that may indicate movement (or non-movement) of the patient, presence or absence of the patient, the weight and/or weight distribution of the patient, or a condition of the patient monitoring system.

Various implementations of the systems and methods described above provide a relatively low-cost solution for reducing pressure ulcers in SCI patients and monitoring the weight of SCI patients by prompting and/or monitoring the performance of pressure relieving activities by SCI patients and providing feedback to SCI patients and their caregivers about the patient's pressure relieving activities, the patient's weight, physical activity, and the operability of the patient's support surface. In addition, the systems and methods may provide active feedback in substantially real time to the patient and/or caregiver. A physical therapist or other caregiver may use the feedback from the system to better understand what physical movements work well for the patient and how compliant the patient is with a physical regimen assigned by the physical therapist or caregiver.

The flowchart and block diagrams in the figures illustrate the architecture, functionality, and operation of possible implementations of systems, methods and computer program products according to various implementations of the present invention. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The implementation was chosen and described in order to best explain the principles of the invention and the practical application, and to enable others of ordinary skill in the art to understand the invention for various implementations with various modifications as are suited to the particular use contemplated.

Any combination of one or more computer readable medium(s) may be used to implement the systems and methods described hereinabove. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing.

Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described herein with reference to flowchart illustrations and/or block diagrams of methods, apparatus (systems) and computer program products according to implementations of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

The invention claimed is:

1. A patient activity monitoring system comprising:
   a rigid support pad having generally planar first and second surfaces, the first and second surfaces being substantially parallel to and opposite each other;
   a cushion having an upper surface and a lower surface, the lower surface of the cushion being disposed on the first surface of the support pad, wherein the upper surface of the cushion is disposable below at least a portion of the patient;
   at least three force sensors disposed on the second surface of the rigid support pad;
   a tilt sensor disposed adjacent a central portion of the first or second surface of the rigid support pad; and
   an electronic control unit comprising a memory and a processor, the processor being in electrical communication with the one or more force sensors, the tilt sensor, and the memory, the processor executing instructions stored on the memory, the instructions comprising:
      electronically receiving a force signal from each force sensor, each force signal based on an amount of force exerted by the second surface of the rigid support pad on each force sensor;

electronically receiving one or more tilt signals from the tilt sensor;

comparing at least a portion of the received force signals and at least a portion of the received tilt signals with an expected range of force signals and tilt signals, respectively, associated with performance of a pressure relieving movement;

identifying that the pressure relieving movement is being performed by the patient in response to the portion of received force signals and the portion of received tilt signals being within the expected range of force signals and the expected range of tilt signals, respectively, associated with the performance of the pressure relieving movement; and in response to identifying that the patient performed the pressure relieving movement, storing the identification of the identified pressure relieving movement in the memory.

2. The system of claim 1, wherein the pressure relieving movement comprises one or more of the following: leaning forward, leaning right, leaning left, and tricep push ups.

3. The system of claim 1, wherein the instructions further include identifying whether the patient is disposed on the upper surface of the cushion based on at least a portion of the received force signals.

4. The system of claim 1, wherein the instructions further include measuring a duration of time during which the identified pressure relieving movement is performed and storing the measured duration with the identification of the identified pressure relieving movement in the memory.

5. The system of claim 1, wherein the instructions further include counting a number of times that the identified pressure relieving movement is performed and storing the counted number with the identification of the identified pressure relieving movement in the memory.

6. The system of claim 4, wherein the instructions further include:

comparing the measured duration associated with the identified pressure relieving movement with a respective clinical guideline time associated with the pressure relieving movement; and generating feedback to the patient indicating a level of compliance with the respective clinical guideline.

7. The system of claim 4, wherein the instructions further include wirelessly communicating the duration and the identified pressure relieving movement stored in the memory to a remotely located computing device.

8. The system of claim 1, wherein the instructions further include comparing the differences in the received force signals with a range of acceptable differences for the force signals associated with safe operation of the monitoring system over a predetermined time period, and in response to the differences in the received force signals being outside of the range of acceptable differences for the force signals for the duration of the predetermined time period, generating and communicating a message to the patient and/or caregiver indicating that a weight of the patient is unevenly distributed over the support pad.

9. The system of claim 1, wherein identifying that the pressure relieving movement is being performed comprises:

extracting at least a portion of each received force signal, retrieving corresponding signal portions associated with the pressure relieving movement, comparing the extracted portions with the retrieved signal portions, and in response to the extracted portions being within a particular range of the retrieved signal portions for a particular time period, identifying the patient's movement as being the identified pressure relieving movement.

10. The system of claim 9, wherein the instructions further include identifying the patient's movement as being a hazardous movement if the retrieved signal portions indicate the pressure relieving movement exceeds the particular time period.

11. The system of claim 9, wherein the extracted portion of the force signals comprises one or more of the following features: a mean, standard deviation, entropy, variance, maximum value, number of mean crossings, and mean absolute deviation.

12. A patient activity monitoring system comprising:

a rigid support pad having generally planar first and second surfaces, the first and second surfaces being substantially parallel to and opposite each other;

a cushion having an upper surface and a lower surface, the lower surface of the cushion being disposed on the first surface of the rigid support pad, wherein the upper surface of the cushion is disposable below at least a portion of the patient;

a tilt sensor disposed adjacent a central portion of the first or second surface of the rigid support pad an electronic control unit comprising a memory and a processor, the processor being in electrical communication with the tilt sensor and the memory, the processor executing instructions stored on the memory, the instructions comprising:

electronically receiving one or more tilt signals from the tilt sensor, comparing at least a portion of the received tilt signals with an expected range of tilt signals associated with performance of a pressure relieving movement, in response to the portion of received tilt signals being within the expected range of tilt signals associated with the performance of the pressure relieving movement, identifying that the pressure relieving movement is being performed by the patient, and storing an identification of the identified pressure relieving movement in the memory.

13. The system of claim 12, wherein the instructions further include calculating a duration during which the identified pressure relieving movement is performed, and storing the calculated duration with the identification of the identified pressure relieving movement in the memory.

14. The system of claim 12, wherein the instructions further include counting a number of times that the identified pressure relieving movement is performed in a particular time period and storing the number of times with the identification of the identified pressure relieving movement in the memory.

15. The system of claim 1, wherein the cushion is an air cushion that comprises an air chamber between the upper and lower surfaces of the cushion, the system further comprising an air pressure sensor disposed in fluid communication with the air chamber, and the processor is further configured for electronically receiving an air pressure signal from the air pressure sensor.

16. The system of claim 15, wherein identifying the pressure relieving movement is further based on at least a portion of the received air pressure signals.

17. The system of claim 15, wherein the instructions further include comparing the received air pressure signal with a calibrated range of air pressure signals associated with the cushion when the patient is disposed on the cushion, and in response to the air pressure signal being outside of the range of calibrated air pressure signals and the force signals being within a range of calibrated force signals, identifying the air pressure and force signals as indicating over or under inflation of the air cushion.

18. The system of claim 1, wherein the instructions further include calculating an average of normalized signals from the force sensors to estimate a magnitude of body motion and energy expenditure of the patient, comparing the calculated magnitude to clinical guidelines associated with body motion of the patient, and generating feedback indicating a level of compliance with the clinical guidelines.

19. The system of claim 1, wherein the instructions further include estimating the amount of body motion and energy expenditure of the patient, comparing the estimated amount of body motion and energy expenditure of the patient to clinical guidelines associated with the body motion, and generating feedback indicating a level of compliance with the clinical guidelines.

20. The system of claim 1, wherein the instructions further include prompting the patient to perform at least one pressure relieving movement in response to not identifying that the patient engaged in any pressure relieving movements within a particular time period.

21. The system of claim 5, wherein the instructions further include:
comparing the counted number associated with the identified pressure relieving movement with a respective clinical guideline count associated with the pressure relieving movement; and
generating feedback to the patient indicating a level of compliance with the respective clinical guideline count.

22. The system of claim 5, wherein the instructions further include wirelessly communicating the count and the identification of the identified pressure relieving movement stored in the memory to a remotely located computing device.

* * * * *